United States Patent

Conrad et al.

Patent Number: 5,100,407
Date of Patent: Mar. 31, 1992

[54] MODULAR TRIAL HIP REPLACEMENT SYSTEM

[75] Inventors: Gordon C. Conrad, Emerson; Thomas J. Parchinski, Wanaque, both of N.J.

[73] Assignee: Pfizer Hospital Products Group, Inc., New York, N.Y.

[21] Appl. No.: 577,999

[22] Filed: Sep. 4, 1990

[51] Int. Cl.⁵ ............................ A61F 5/04; A61F 2/30
[52] U.S. Cl. ............................................ 606/79; 623/18
[58] Field of Search .................... 606/53, 60, 62, 63, 606/65, 67, 79, 83, 84, 85, 89; 623/18

[56] References Cited

U.S. PATENT DOCUMENTS

| | | | |
|---|---|---|---|
| 3,918,441 | 11/1975 | Getscher | 606/64 |
| 3,943,576 | 3/1976 | Sivash | 623/18 |
| 3,987,499 | 10/1976 | Scharbach | 606/72 |
| 4,587,964 | 5/1986 | Walker | 606/85 |
| 4,676,797 | 6/1987 | Anapliotis | 623/18 |
| 4,705,520 | 11/1987 | Ahrens | 623/18 |
| 4,728,333 | 3/1988 | Masse | 606/63 |
| 4,846,839 | 7/1989 | Noiles | 623/18 |
| 4,911,722 | 3/1990 | Crespy | 623/18 |
| 4,936,863 | 6/1990 | Hofmann | 606/66 |
| 4,963,155 | 10/1990 | Lazzeri | 606/85 |

OTHER PUBLICATIONS

P. D-9 from 1982 Howmedica Catalog.

Primary Examiner—Robert A. Hafer
Assistant Examiner—Michael Brown
Attorney, Agent, or Firm—Peter C. Richardson; Lawrence C. Akers; Raymond W. Augustin

[57] ABSTRACT

A multi-piece trial femoral component kit is used for preparing and sizing a femoral cavity prior to implantation of a prosthetic femoral component. The trial component kit has at least three trial stem portions of differing size and at least three trial body portions of different size. The stem and body portions include mating male and female elements which allow the stem portions to be securely coupled to the body portions. In order to ensure that the so-coupled stem and body portions form a trial femoral component having a size equal to an available orthopedic femoral implant, the male and female elements include a key and keyway which are sized so that only trial stem and body portions resulting in an available femoral implant can be combined and used as a trial femoral component.

20 Claims, 5 Drawing Sheets

MODULAR TRIAL HIP REPLACEMENT SYSTEM

BACKGROUND OF THE INVENTION

1. Field of the Invention

This invention relates to an orthopedic trial femoral component for use in determining the correct prosthetic femoral component for implantation from a group of prosthetic femoral components. These implants are utilized in replacing the head and neck of a femur with a prosthetic part. More particularly, this invention relates to a two-piece trial component which can be used to guide the surgeon in resecting a damaged femur head and neck and replacing it with a prosthetic femoral component of the proper size.

2. Description of the Prior Art

A surgical operation to replace the femur head and neck with a prosthetic femoral component is a complex operation and requires a relatively long time. There has been a long felt need for methods to simplify and shorten this surgery. This is especially true since many of the patients requiring such surgery are elderly, frail or otherwise sick and cannot withstand long operations. In addition, in the trauma area, most individuals needing a femur head/neck replacement are multitrauma patients who require a series of surgical operations performed by different surgeons.

In all these examples, the longer the patient is under anesthesia, the greater the risk to the health of the patient. In the past as a guide during surgery, surgeons used a series of one-piece trail prostheses, which trail prostheses were identical in size to the corresponding prosthetic implants. Normally, prosthetic femoral component implants come in discrete sizes, which sizes have been determined to cover the widest range of patients surgeons are likely to encounter. Since the human femur varies markedly in size, orthopedic implant manufacturers have provided individual femoral component implants sized to cover a range of different sized individuals. Usually, the surgeon examines X-rays to determine the approximate size femoral prosthesis, from a discrete group of sizes, which would be required. He then uses the corresponding trial component as a guide to prepare the femur to receive the prosthesis chosen.

Often, however, the surgeon finds upon implantation that either his preparation of the femur was incorrect or that the three dimensional body geometry does not allow for the incorporation of the preliminarily chosen femoral component. Manufacturers compensate for these problems by providing femoral prosthesis components with identical stem lengths but different neck/body sizes or vice versa. In the prior art systems the surgeon has a series of one-piece trial components with multiple stem and body sizes. Each one-piece trial component will have a body portion of predetermined size attached to it. The surgeon then uses trial and error selection of trial prostheses to determine the best fitting component.

Since in the past manufacturers have supplied a trial component corresponding to each of a plurality of femoral prostheses, the surgeon must attempt to get a trial stem to fit so that his final component will likewise be correctly sized. This is difficult because the surgeon cannot view the medullary canal fit of a trial stem in a one-piece trial component because the proximal body block his view. Thus the surgeon must ream and/or rasp the femoral canal until, through feel and guesswork, he thinks the trial stem fits. However, especially in cemented applications, it is difficult for the surgeon to see the gap created by his reaming and thus determine the actual gap to be filled by the bone cement.

In a one-piece trial component, when the surgeon puts the trial stem into the bone, the proximal body tries to seat on the free-hand cut made by the surgeon in the femoral neck area at the start of the operation. Normally this cut is a 90° L-shaped cut, removing the head and neck of the natural femur. While working on the fit of the distal stem portion, the surgeon may actually contact a bony obstruction at the proximal end of the femur with the body portion of the trial prosthesis. At this point, it is extremely difficult to discern whether the problem is located distally around the stem or proximally around the body portion of the trial prosthesis. If the problem is in the proximal area of the bone, then the surgeon must re-cut the proximal 9° surface. This process may have to be repeated a number of times to make the trial component fit correctly both in the distal stem area and in the proximal body area.

By use of the present invention, it has been found that the problems with the prior are surgical techniques can be overcome. Specifically, in the present invention, the distal stem and proximal body portions of the femoral component are fitted separately. To this end, the present invention provides a two-piece trial component kit with a plurality of interchangeable heads and stems. With the system of the present invention, the surgeon may either address the distal stem fit or the proximal body fit first. More importantly, the surgeon can address each fit distinctly and independently, i.e., the stem portion separately from the proximal body portion.

In the preferred embodiment of the present invention, the trial body portion is provided with 90° guide surfaces for either purposes of checking the accuracy of the right angle cut or to be utilized as a saw blade guide surface. In the preferred surgical method, the surgeon first prepares the proximal femur, making the 90° cut in a rough fashion and takes the trial proximal body and completely checks the accuracy of his right angle proximal cut. The surgeon may also use the trial body guide surfaces as a saw guide. Since the stem is not attached to the trial body portion at this time, the surgeon can easily check the accuracy of his cut. Having quickly and accurately created a bone bed for the proximal body portion, he can then move on to the distal trial stem portion and fit the stem to the femoral canal.

To accomplish this the surgeon will first insert various trial stem sizes to see which fits the patient best. If a stem fits well without any bone excavation in the femoral canal, he can quickly move ahead to the next phase of the operation. If he does need to prepare the femoral canal using rasps and/or reamers, he can quickly asses the stem fit and, if necessary, prepare the bone quickly because he can clearly see the stem within the femoral canal. This would not be possible with a one-piece trial because the integral head/body would obstruct his view.

Next, the surgeon attaches the trial stem chosen with the appropriate proximal body trial portion and places the assembled trial unit into position within the bone. At the time the surgeon implants an assembled two-piece trial, the fit has been determined and merely has to be checked. After checking, the surgeon seats the corresponding sized implant into the femur.

Because the surgeon has available a predetermined number of prostheses having different body and stem sizes, some of which overlap, it is imperative that the trial body portion and the trial stem portion chosen for the sizing operation correspond to a femoral component size available. In a preferred two-piece trial component system of the present invention, each piece has a male and female element for coupling the two pieces together which includes a key mechanism that, if the combination stem and body produces an available prosthesis size, mates, but if there is no available prosthesis size, does not mate. Consequently, the surgeon knows at the time of trial that he will not be able to find a femoral prosthetic component for implantation matching the trial component.

SUMMARY OF THE INVENTION

It is an object of the invention to provide a two-piece trial femoral component to be used in determining the correct prosthetic femoral component for implantation into a femur from a group of prosthetic femoral components.

It is an additional object of this invention to provide a two-piece trial femoral component which can be used as a guide in resecting the head of a femur and implanting a prosthetic femoral component of the proper size therein.

It is yet a further object of the invention to provide a two-piece trial femoral component having a body and stem portion wherein only trial bodies and stems can be combined which result in a trial component corresponding to an available prosthetic femoral component.

These and other objects of the present invention are provided in a preferred embodiment of the invention which includes a multi-piece trial femoral component kit for use in preparing and sizing a femoral cavity prior to implantation of a prosthetic femoral component. The trial component kit includes at least two trial stem portions of different size and at least two trial proximal body portions of different size. The trial stem and body portions may be coupled to produce a trial femoral component which can be used as a guide for correctly sizing the cavity within a femur for implantation of a prosthetic femoral component. Each body portion includes two generally perpendicular guide surfaces thereon for use in resecting the head of the femur during the operation. One of these two generally perpendicular guide surfaces aligns in a plane parallel to an anterior-posterior plane through the femoral cavity.

Each trial body portion and trial stem portion includes a mating male-female element which is utilized to couple the two piece together. One of the male-female elements includes a spring detent so that the two-piece trial femoral component can be held together to form a one-piece component but can be selectively separated so that more than one body portion can be coupled to each stem portion or vice-versa. Each male or female element includes a key or keyway sized to allow selected body portions to be coupled to selected stem portions. This is done to ensure that the surgeon can only form a two-piece trial femoral component which corresponds to a prosthetic orthopedic implant available at the operation site. One of the body of stem trial portions also includes a spring detent used to selectively releasably secure the trial body portion to the trial stem portion.

These and other objects and advantages of the present invention will become apparent from the following description of the accompanying drawings, which disclose one embodiment of the invention. It is to be understood that the drawings are to be used for purposes of illustration only, and not as a definition of the invention.

BRIEF DESCRIPTION OF THE DRAWINGS

In the drawings, wherein similar reference characters denote similar elements throughout the views.

DESCRIPTION OF THE PREFERRED EMBODIMENT

Referring to FIGS. 1-4, there is shown a two-piece trial femoral component of the present invention generally denoted as 10. Trial femoral prosthesis 10 is composed of a distal trial stem portion 12 and a proximal trial body portion 14. Body portion 14 includes two generally perpendicular guide surfaces 16 and 18 which serve to guide the saw blade used by the surgeon during the resecting of the head/neck area of the femur or to be used to check a free-hand cut. Trial body 14 also includes a trunion 20 which is used to mount a spherical head (not shown) and an opening 22 designed to accommodate a tool (not shown) capable of being mated to body portion 14 to facilitate insertion and removal of the trial component.

Figures 3, 4:
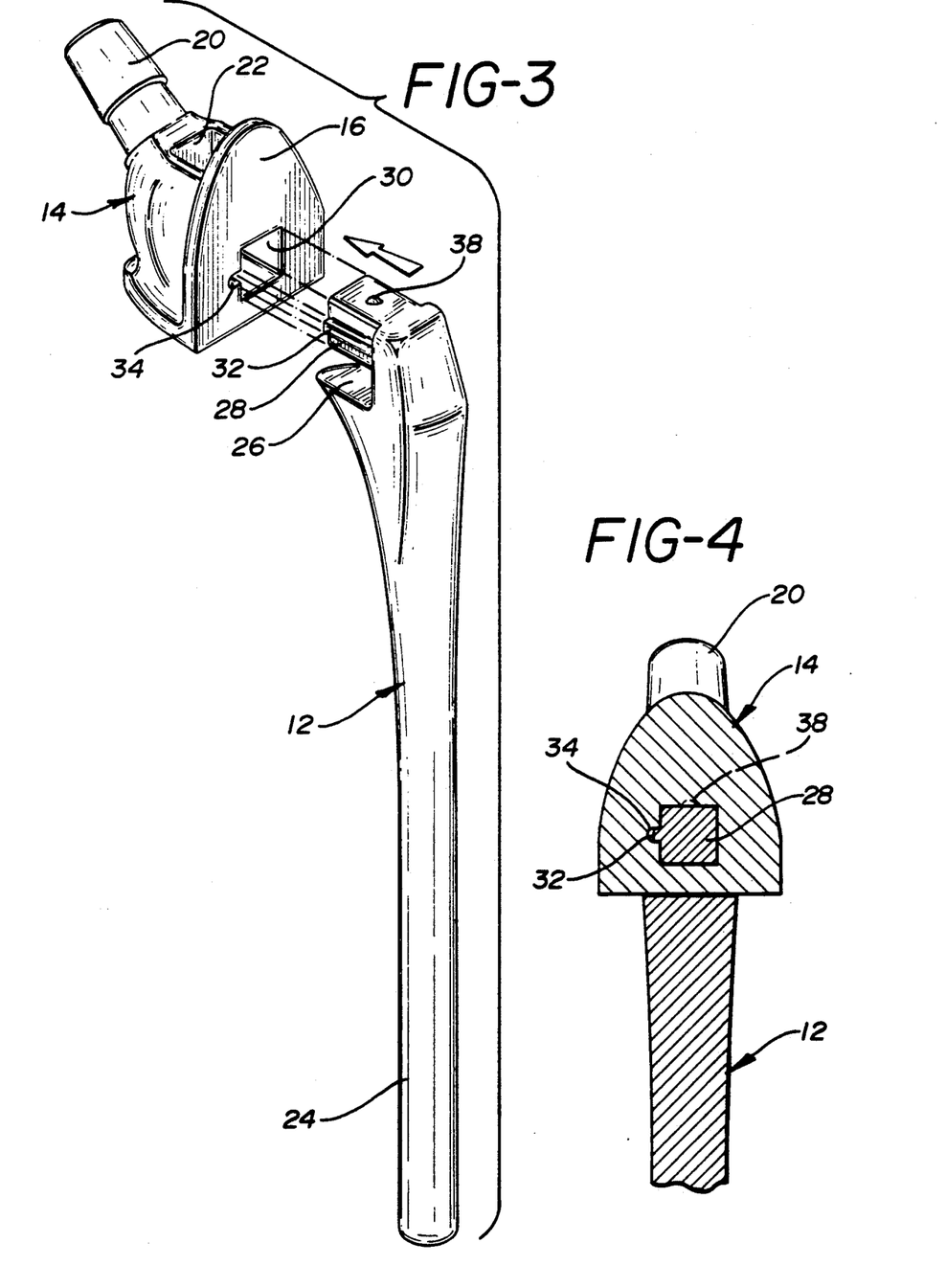
FIG. 3 is an exploded view of the femoral component of FIG. 1 showing the trial body portion separated from the trial stem portion.
FIG. 4 is a cross-sectional view of the trial femoral component of FIG. 1 along lines 4—4.

As can be best seen in FIG. 3, trial stem 12 has a distal portion 24 adapted to be received within the medullary canal of the femur. At its proximal end 26 trial stem 12 has a male element 28 which is adapted to be inserted within a corresponding opening 30 in surface 16 of body 14. Male element 28 includes at least one key element 32 designed to engage a corresponding keyway 34 in body 14.

Figures 1, 2:
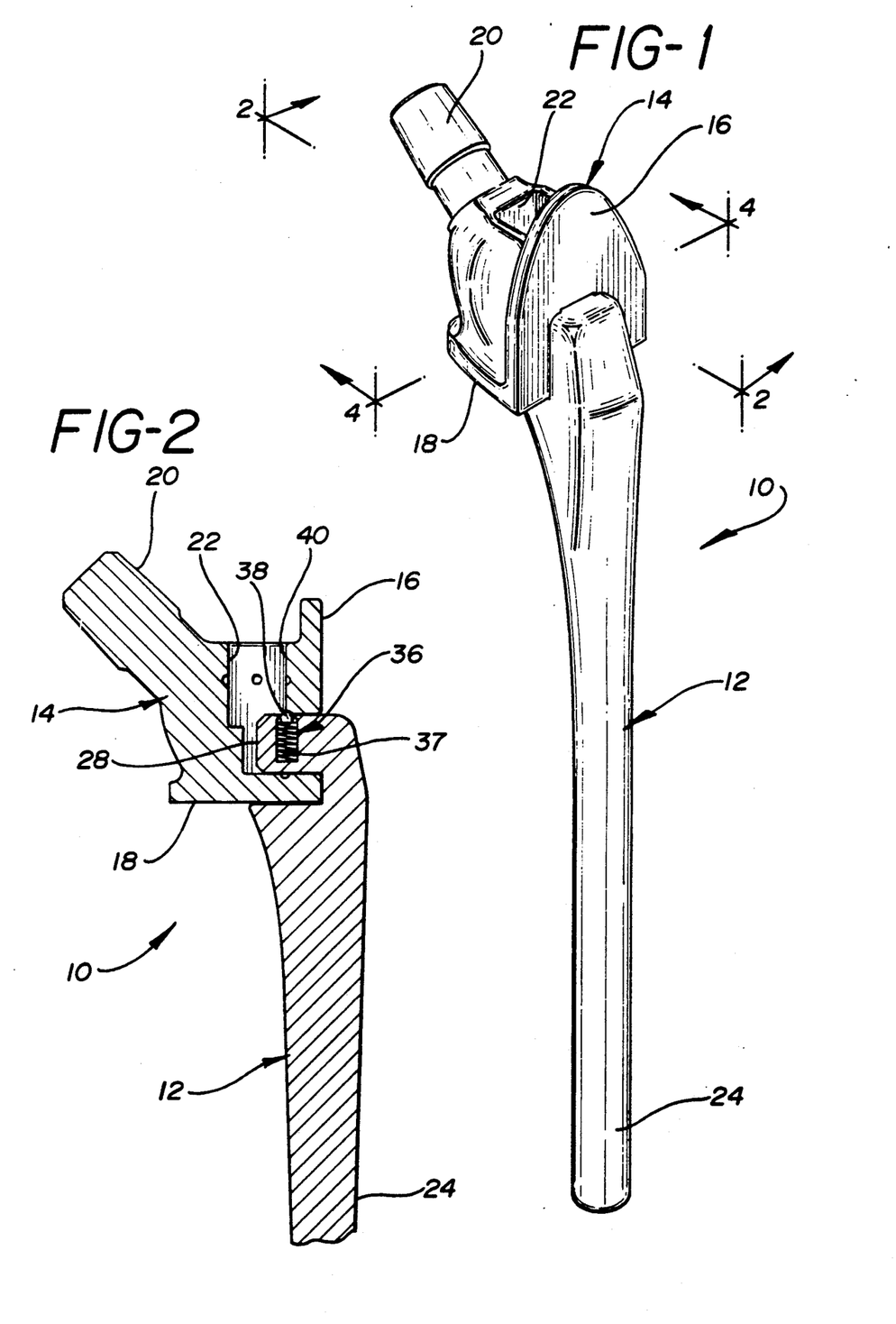
FIG. 1 is an isometric view of the trial femoral component of the present invention.
FIG. 2 is a cross-sectional view of the femoral component of FIG. 1 along the lines 2—2.

Referring to FIG. 2, there is shown a spring and ball detent 36 designed to releasable couple stem 12 to body 14. A ball 38 is depressed as male element 28 is slid within corresponding female element 30 and then springs up once the inner wall 40 of tool opening 22 is reached. Spring 37 is sized so that a predetermined amount of hand pressure tending to separate body 14 from stem 12 depresses ball 38 and allows the two-piece trial prosthesis to be uncoupled.

Figure 8:
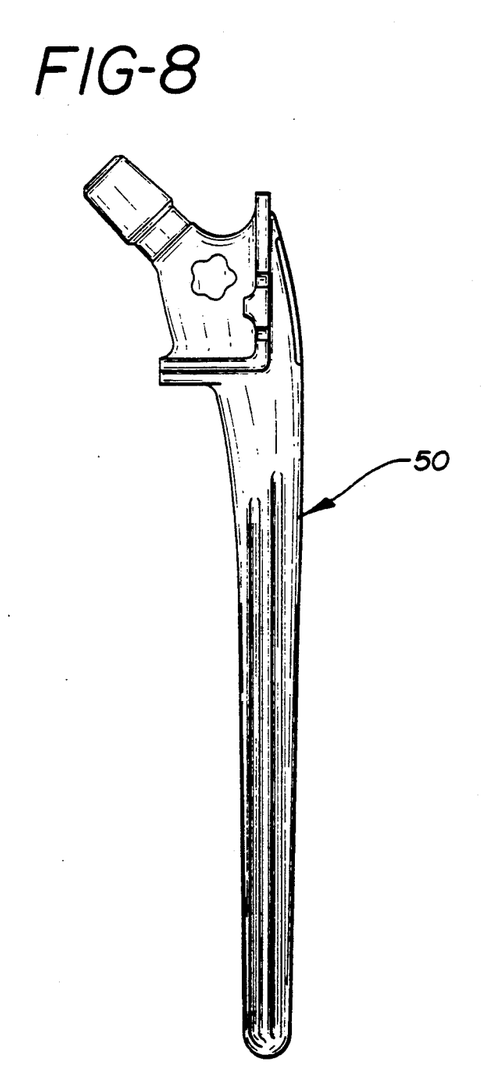
FIG. 8 is an elevation view of the prosthetic femoral implant corresponding in size to the trial femoral component of FIG. 5.
Figure 9:
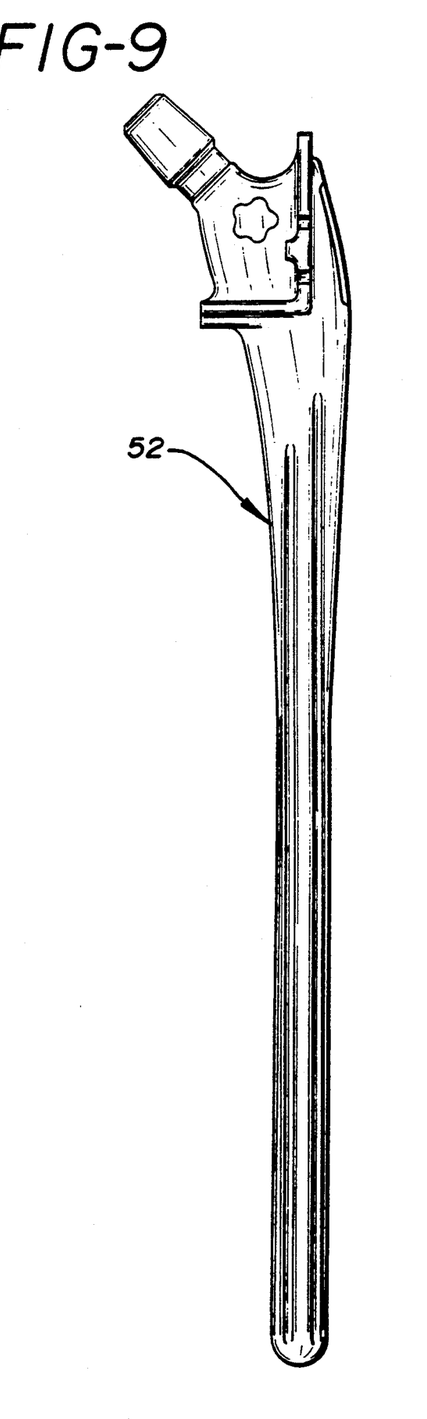
FIG. 9 is an elevation view of the prosthetic femoral component corresponding in size to the two-piece trial femoral component shown in FIG. 7.

Referring to FIGS. 5-7A, there is shown three trial body components generally denoted as 14', 14" and 14'" respectively and three stem components denoted as 12', 12" and 12'" respectively. Each body portion 14', 14", 14'" is of different size and similarly the three trial portions 12', 12" and 12'" are also of three different sizes. Each stem 12', 12", 12'" includes a male element 28', 28", 28'" respectively adapted to fit in any body 14', 14" and 14'". However, because orthopedic implant manufacturers supply only a discrete number of femoral component implants with a limited number of different body and stem sizes, it is necessary to ensure that only a trial prosthesis having a body and stem size corresponding to an actual implantable prosthesis can be produced by interchanging various stems 12', 12", 12'" and bodies 14', 14" and 14'". Two such prostheses denoted as 50 and 52 are shown in FIG. 8 and FIG. 9.

In order to achieve this end in the preferred embodiment, body 14' has a keyway on the left hand side of female element 30 and body 14'" has keyway 34'" only on the right hand size of opening 30'". Body 14" includes keyways 34" on either side of opening 30".

Figure 5:
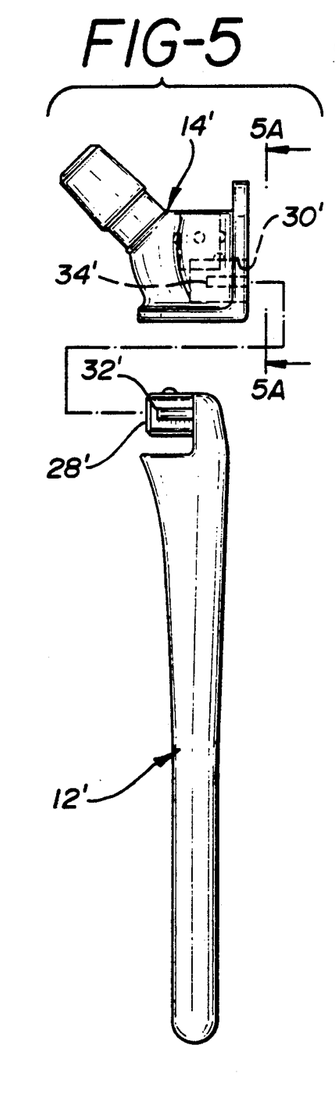
FIG. 5 is an elevation view of a small size trial femoral component with the body and stem separated.
Figure 5A:
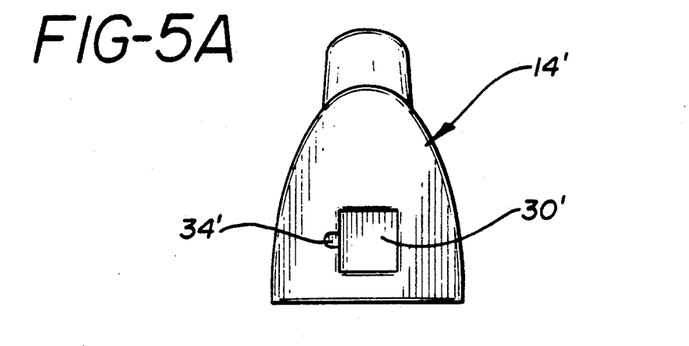
FIG. 5A is a cross-sectional view of the body portion of FIG. 5 along lines 5A—5A.
Figures 6, 7:
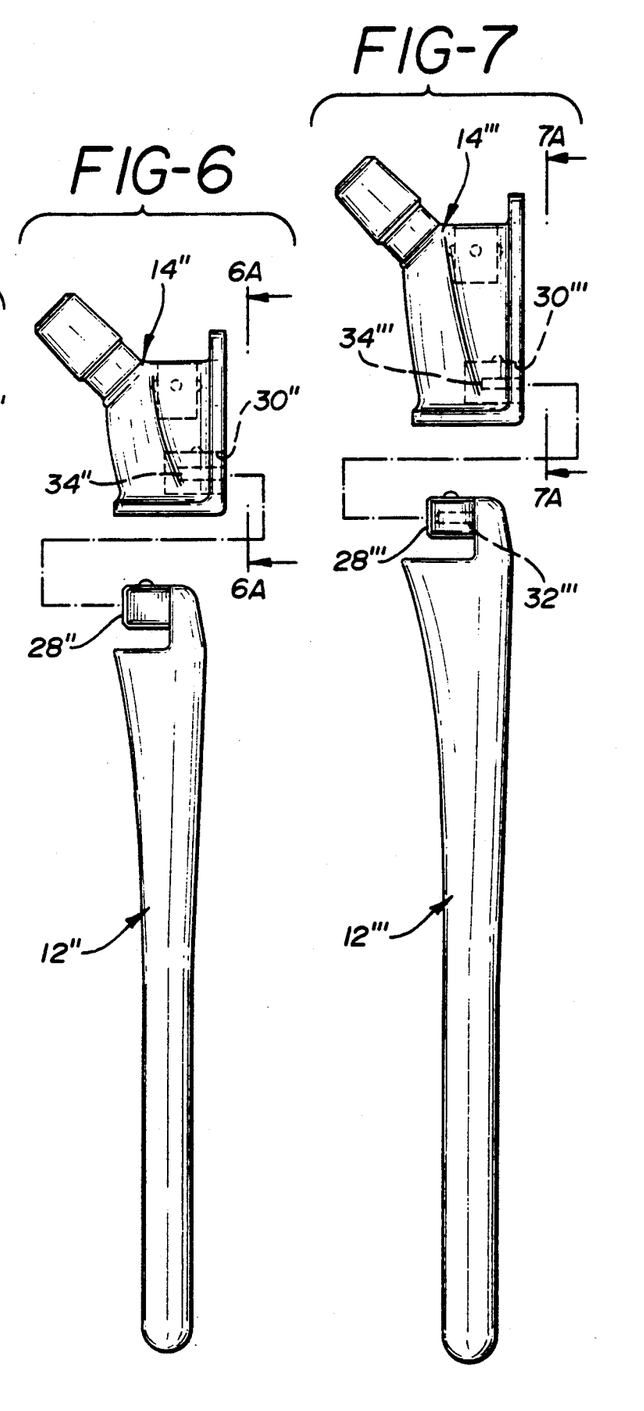
FIG. 6 is an elevation view of a trial femoral component of the present invention being larger in size than that shown in FIG. 5.
FIG. 7 is an elevation view of a two-piece femoral component of the present invention being larger in size than that shown in FIG. 36.
Figure 6A:
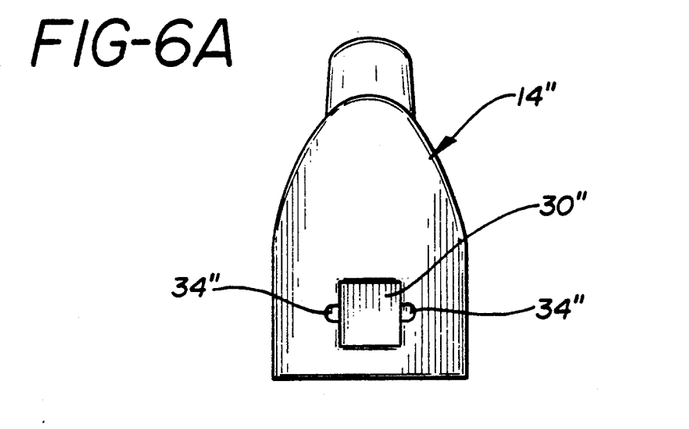
FIG. 6A is a cross-sectional view of the body portion of FIG. 6 along lines 6A—6A.
Figure 7A:
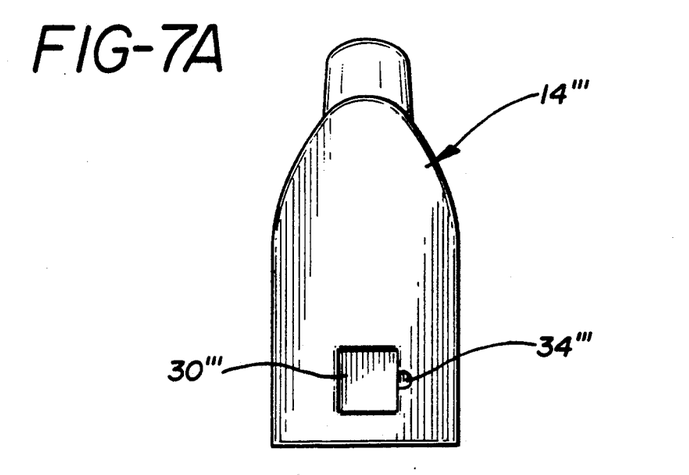
FIG. 7A is a cross-sectional view of the body component of FIG. 7 along lines 7A—7A.

Corresponding stem 12' includes a key 32' on its right hand side while stem 12" has no key and stem 12'" has a key only on the right hand side thereof. Thus it can be seen that stem 12' cannot be coupled to body 14'" and, likewise stem 12'" cannot be coupled to body 14'. Stem 12" and body 14" may be either coupled to one another or coupled to stem 12', 12'" in the case of body 14" and body 14' and 14'" in the case of stem 12".

As can be seen from above, the preferred embodiment of the trial component kit of the present invention, actual femoral prosthetic implants are available only in the combinations set forth above. In other words, in the preferred embodiment there would be no prosthetic femoral component available for implantation corresponding in size to a body 14' coupled to a 12'" stem. Likewise, femoral prosthetic implantable components (such as those shown by way of example in FIGS. 8 and 9 and numbers 50, 52 respectively) would not be available in a 14'" body with a 12' stem, but a prosthetic component would be available for 14' and 12' (FIG. 8) and 14'" and 12'" (FIG. 9). Clearly, trial body and stem portions of larger, smaller or intermediate sizes to those shown in FIGS. 5, 6 and 7 can be added to the kit. However, keys and keyways of different location or size must be included to preclude the formation of a trial prosthesis size which does not correspond to an actual femoral component available for implantation.

In the preferred embodiment, each body 14' through 14'" and each stem 12' through 12'" includes sizes printed thereon which corresponds to the size of available prosthetic femoral component implants. Thus a surgeon can choose a two-piece trial prosthesis and determined which of a number (usually a dozen or more) of implants he should employ. Clearly, the surgeon can mix and match until he obtains a proper fit, always knowing that he cannot form a trial component which does not correspond to an actual implant he has available. It can be seen that other methods other than use of a key and keyway can be utilized to ensure that mismatched trial bodies and stems cannot be combined.

The process of utilizing the trial component kit of the present invention will now be described. Initially, the surgeon is supplied with a limited number of femoral prosthetic components for implantation into the femur. He is then supplied with a series of trial body portions, one corresponding in size to each size body portion on an implantable prosthesis. Likewise, he is supplied with a group of stem portions corresponding in size to stems provided on the implantable prosthetic femoral components. In the preferred surgical method, the surgeon first prepares a proximal femur, which is normally the case, making a 90° cut utilizing surfaces 16 or 18 of trial body 14 either as a saw guide or as a means to check a 90° C. free-hand cut. Since stem 12 is not attached to the trial body portion 14 at this time, the surgeon can easily check the accuracy of his cut.

The surgeon may now prepare the intramedullary canal of the femur with the use of a trial stem portion 12. To accomplish this the surgeon will first insert various trial stem sizes such as 12', 12", 12'" to see which fits the patient best. If a stem size fits well without any bone excavation in the femoral canal, he can quickly move ahead to the next phase of the operation. If none of the trial stem sizes fit adequately, the surgeon then prepares the femoral canal using rasps and/or reamers, as is well known. The surgeon can then quickly asses the fit of stem 12 and, if necessary, prepare the bone quickly because he can clearly see the stem within the femoral canal as body portion 14 is not attached thereto at this point.

Next the surgeon attaches the trial stem 12 chosen with the chosen proximal body portion 14 and places the assembled unit into position within the bone. Since the available sizes of prosthetic femoral components (such as 50, 52) have been chosen to cover a vast majority of patients, it is highly unlikely that there will be no correctly sized trial body 14 available for chosen stem 12, i.e. it is very unlikely that a patient would need a large stem (such as 12'") and a small size body (such as 14'). The units may be assembled by sliding male element 28 into female opening 30 causing ball 38 to be pressed downward and then moving upward and engaging surface 40 to thereby lock body portion 14 to stem 12. The surgeon then places the assembled trial unit into position within the bone, places the spherical ball (not shown) on trunion 20 to check the alignment thereof within the acetabulum. After checking, the surgeon merely removes the trial prosthesis and seats the correspondingly sized implant, such as 50, 52, into the femoral canal.

As described above, a key system 32, 34 is utilized to ensure that only trial components corresponding to the limited number of implantable femoral prosthetic components such as 50, 52 can be formed.

If, during the operation, the surgeon determines that the trial body portion or trial stem portion is incorrect, he may uncouple the two-piece trial femoral component 10 by merely exerting pressure against surface 16 while holding stem 12 in place. Spring 37 is sized so that only a reasonable force is necessary to uncouple body portion 14 from stem 12.

Referring to FIGS. 8 and 9, it can be seen that the actual femoral implants 50, 52 are of a one-piece design and each has perpendicular seating surfaces 54 and 56. Star-shaped through holes 58 and recesses 60 are provided so that the prosthesis may be wired to the femur.

While only several embodiments and examples of the present invention have been described, it is obvious that many changes and modifications may be made thereunto, without departing from the spirit and scope of the invention.

We claim:

1. A multi-piece trial femoral component kit for use in selecting a prosthetic femoral component and preparing and sizing a femoral cavity prior to implantation of a prosthetic femoral component, the trial component kit comprising:
    at least two trial distal stem portions of different size;
    at least two trial proximal body portions of different size, said body portions each having two generally perpendicular resection guide surfaces thereon with a first of said two generally perpendicular guide surfaces being aligned in a plane extending transversely to the femoral cavity in the area of the femoral neck and a second of said guide surfaces extending proximally from said first guide surface; and
    means for coupling said trial body portions to said trial stem portions, said means for coupling including a means for preventing selected trial stem portions of said at least two stem portions from being coupled to selected trial body portions of said at least two body portions.

2. The multi-piece trial femoral component kit set forth in claim 1 wherein said means for coupling said body and stem portions include mating male and female elements integrally formed on respective body and stem portions.

3. The multi-piece trial femoral component kit as set forth in claim 1 wherein said means for preventing said selected trial body portions from coupling with said selected trial stem portions is a key mechanism with a nonengagable key and keyway located on respective male-female elements of said selected trial body and stem portions.

4. The multi-piece trial femoral component kit as set forth in claim 1 wherein said means for coupling said trial body portion to said trial stem portion leaves a major portion of each of said two generally perpendicular guide surfaces exposed after coupling said trial body portion with said trial stem portion.

5. The multi-piece trial femoral component kit as set forth in claim 1 wherein said means for coupling permits coupling said trial body portion to said trial stem by movement of said body portion in a direction transverse to the longitudinal axis of said stem.

6. A two-piece trial femoral component for use in selecting a prosthetic femoral component and sizing and preparing a femoral cavity prior to implantation of the selected prosthetic implant comprising:
    a trial stem portion;
    a trial body portion removably connected to said stem portion, said trial body portion having two generally perpendicular resection guide surfaces thereon with one of said two generally perpendicular guide surfaces being aligned in a plane transverse to the femoral cavity in the area of the femoral neck and a second of said guide surfaces extending proximally from said first guide surface; and
    selectively releasable means for securing said removable trial body portion to said trial stem portion.

7. The two-piece trial femoral component as set forth in claim 6 wherein said selectively releasable means for holding said removable body portion to said stem includes mating male and female elements integrally formed on respective body and stem portions.

8. The two-piece trial femoral component as set forth in claim 7 wherein one of said mating male and female elements includes a key and the other of said male and female elements includes a mating keyway.

9. The two-piece trial femoral component as set forth in claim 8 wherein one of said male and female elements includes a selectively releasable spring detent for securing said body portion to said stem portion.

10. The multi-piece trial femoral component kit as set forth in claim 6 wherein said means for coupling said trial body portion to said trial stem portion leaves a major portion of each of said two generally perpendicular guide surfaces exposed after coupling said trial body portion with said trial stem portion.

11. The multi-piece trial femoral component kit as set forth in claim 6 wherein said means for coupling permits coupling said trial body portion to said trial stem by movement of said body portion in a direction transverse to the longitudinal axis of said stem.

12. A multi-piece trial femoral component kit for use in selecting a prosthetic femoral component and preparing and sizing a femoral cavity prior to implantation of a prosthetic femoral component chosen from a limited number of prosthetic femoral components, the trial component kit comprising:
    at least three trial stem portions of different size;
    at least three trial body portions of different size, said body portions each having two generally perpendicular resection guide surfaces thereon with one of said two generally perpendicular guide surfaces being aligned in a plane transverse to the femoral cavity in the area of the femoral neck and a second of said guide surfaces extending proximally from said first guide surface; and
    means for coupling said trial body portions to said trial stem portion, said means for coupling including a means for allowing at least one stem portion of said at least three stem portions to couple with at least two body portions of said at least three body portions.

13. The kit as set forth in claim 12 wherein said means for coupling said body and stem portions include mating male and female elements integrally formed on respective body and stem portions.

14. The kit as set forth in claim 13 wherein one of said mating male and female elements includes a key and the other of said male and female elements includes a keyway.

15. The kit as set forth in claim 14 wherein one of said male and female elements includes a selectively releasable spring detent for securing said body portion to said stem portion.

16. The kit as set forth in claim 12 wherein said means for allowing at least one trial body portions of said at least three trial body portions to be coupled to at least two trial stem portions of said at least three trial stem portions only permits formation of a trial femoral component having a size corresponding to a predetermined stem and body size of said limited number of prosthetic femoral components.

17. The kit as set forth in claim 16 wherein said means for allowing said selected trial body portions to couple with said selected trial stem portions is a key mechanism with a nonengagable key and keyway located on respective selected trial body and stem portions.

18. The kit as set forth in claim 12 wherein the means for coupling said selected trial stem portions and said selected trial body portions of said plurality of trial stem and body portions is a key mechanism with a mating key and keyway located on respective selected trial body and stem portions.

19. The multi-piece trial femoral component kit as set forth in claim 12 wherein said means for coupling said trial body portion to said trial stem portion leaves a major portion of each of said two generally perpendicular guide surfaces exposed after coupling said trial body portion with said trial stem portion.

20. The multi-piece trial femoral component kit as set forth in claim 12 wherein said means for coupling permits coupling said trial body portion to said trial stem by movement of said body portion in a direction transverse to the longitudinal axis of said stem.

* * * * *